(12) United States Patent
Seddon et al.

(10) Patent No.: US 11,896,462 B2
(45) Date of Patent: Feb. 13, 2024

(54) HIGHLY CONFORMABLE WOUND DRESSING

(71) Applicant: KCI Licensing, Inc., San Antonio, TX (US)

(72) Inventors: James Killingworth Seddon, Wimborne (GB); Colin John Hall, Poole (GB)

(73) Assignee: 3M Innovative Properties Company, Saint Paul, MN (US)

( * ) Notice: Subject to any disclaimer, the term of this patent is extended or adjusted under 35 U.S.C. 154(b) by 468 days.

(21) Appl. No.: 16/438,017

(22) Filed: Jun. 11, 2019

(65) Prior Publication Data
US 2020/0000985 A1 Jan. 2, 2020

Related U.S. Application Data

(60) Provisional application No. 62/691,410, filed on Jun. 28, 2018.

(51) Int. Cl.
*A61F 13/00* (2006.01)
*A61M 1/00* (2006.01)

(52) U.S. Cl.
CPC ......... *A61F 13/00029* (2013.01); *A61M 1/79* (2021.05); *A61M 1/915* (2021.05); *A61M 1/78* (2021.05); *A61M 1/80* (2021.05); *A61M 1/92* (2021.05); *A61M 2205/18* (2013.01); *A61M 2205/3344* (2013.01);
(Continued)

(58) Field of Classification Search
CPC ............ A61M 1/90; A61M 1/79; A61M 1/78; A61M 1/80; A61M 2205/18; A61M 2205/3344; A61M 2205/3351; A61M 2205/581; A61M 2205/583;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Toshibumi Takahashi, Wound protective material, Oct. 30, 2008 (Year: 2008).*

(Continued)

*Primary Examiner* — Kai H Weng
*Assistant Examiner* — Nhu Q. Tran

(57) ABSTRACT

In some examples, a dressing filler for treating a tissue site may include a plurality of filler elements and a tissue interface layer. Each of the filler elements may include a first surface and a second surface opposite the first surface and separated from the first surface by a thickness. The tissue interface layer may include a first side configured to be positioned facing the tissue site and a second side positioned opposite the first side. The first surface of each of the filler elements may be coupled to the second side of the tissue interface layer. Also provided are other apparatuses, dressings, systems, and methods suitable for treating a tissue site.

34 Claims, 11 Drawing Sheets

(52) U.S. Cl.
CPC .............. *A61M 2205/3351* (2013.01); *A61M 2205/581* (2013.01); *A61M 2205/583* (2013.01); *A61M 2205/8206* (2013.01)

(58) Field of Classification Search
CPC ...... A61M 2205/8206; A61F 13/00068; A61F 13/00029
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0270827 A1* | 10/2009 | Gundersen .......... A61F 13/0209 156/78 |
| 2009/0299342 A1* | 12/2009 | Cavanaugh ........... A61F 15/008 604/543 |
| 2010/0004611 A1 | 1/2010 | Aali |
| 2010/0160874 A1* | 6/2010 | Robinson ................ A61M 1/90 604/313 |
| 2012/0053539 A1 | 3/2012 | Olson et al. |
| 2014/0163491 A1 | 6/2014 | Schuessler et al. |
| 2015/0080788 A1 | 3/2015 | Blott et al. |
| 2016/0339158 A1* | 11/2016 | Collinson ........... A61F 13/0216 |
| 2020/0197227 A1* | 6/2020 | Locke ................. A61F 13/0206 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |

(56) References Cited

FOREIGN PATENT DOCUMENTS

| | | |
|---|---|---|
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2008259629 A * | 10/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009158500 A2 | 12/2009 |
| WO | 2014140578 A1 | 9/2014 |
| WO | 2017119996 A1 | 7/2017 |
| WO | 2019084006 A1 | 5/2019 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. @ Therapy Clinical Guidelines: A Reference Source for Clinicians; Jul. 2007.

International Search Report and Written Opinion for Corresponding Application No. PCT/US2019/036585, dated Sep. 12, 2019.

* cited by examiner

HIGHLY CONFORMABLE WOUND DRESSING

RELATED APPLICATIONS

The present application claims the benefit, under 35 USC § 119(e), of the filing of U.S. Provisional Patent Application Ser. No. 62/691,410, entitled "A Highly Conformable Wound Dressing," filed Jun. 28, 2018, which is incorporated herein by reference for all purposes.

TECHNICAL FIELD

The invention set forth in the appended claims relates generally to tissue treatment systems and more particularly, but without limitation, to a highly conformable dressing or wound filler that may be suitable for use with negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

SUMMARY

New and useful systems, apparatuses, and methods for treating a tissue site in a negative-pressure therapy environment are set forth in the appended claims. Illustrative embodiments are also provided to enable a person skilled in the art to make and use the claimed subject matter.

For example, in some embodiments, a conformable dressing for treating a tissue site may include a plurality of discrete manifold members and a carrier. Each discrete manifold member may include a first surface and a second surface. The first surface may be separated from the second surface by a perimeter wall. The carrier may include a first side configured to be positioned facing the tissue site and a second side positioned opposite the first side. The first surface of each of the discrete manifold members may be coupled to the second side of the carrier.

Further, in some embodiments, a system for treating a tissue site may include the conformable dressing described above, and additionally, the system may include a sealing member and a reduced pressure source. The sealing member may be configured to cover the dressing and to create a sealed space at the tissue site. The reduced pressure source may be configured to be coupled in fluid communication with the sealed space.

In other example embodiments, a dressing filler for treating a tissue site may include a plurality of filler elements and a tissue interface layer. Each of the filler elements may include a first surface and a second surface opposite the first surface and separated from the first surface by a thickness. The tissue interface layer may include a first side configured to be positioned facing the tissue site and a second side positioned opposite the first side. The first surface of each of the filler elements may be coupled to the second side of the tissue interface layer.

A method is also described herein, wherein in some example embodiments a method for treating a tissue site may include providing a conformable dressing comprising a plurality of discrete manifold members coupled to a stretchable carrier. The plurality of discrete manifold members may be separated from one another along an exterior border. Further, the method may include positioning the conformable dressing into conformity with tissue at the tissue site. At least a portion of the stretchable carrier may be positioned in a stretched state when the conformable dressing is conformed to the tissue site. Further, the method may include covering the conformable dressing with a sealing member to form a sealed space at the tissue site. Further, the method may include applying reduced pressure to the sealed space.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments enables a person skilled in the art to make and use the subject matter set forth in the appended claims. Certain details already known in the art may be omitted. Therefore, the following detailed description is illustrative and non-limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as recognized by those skilled in the art, this frame of reference is merely a descriptive expedient rather than a strict prescription.

Figure 1:
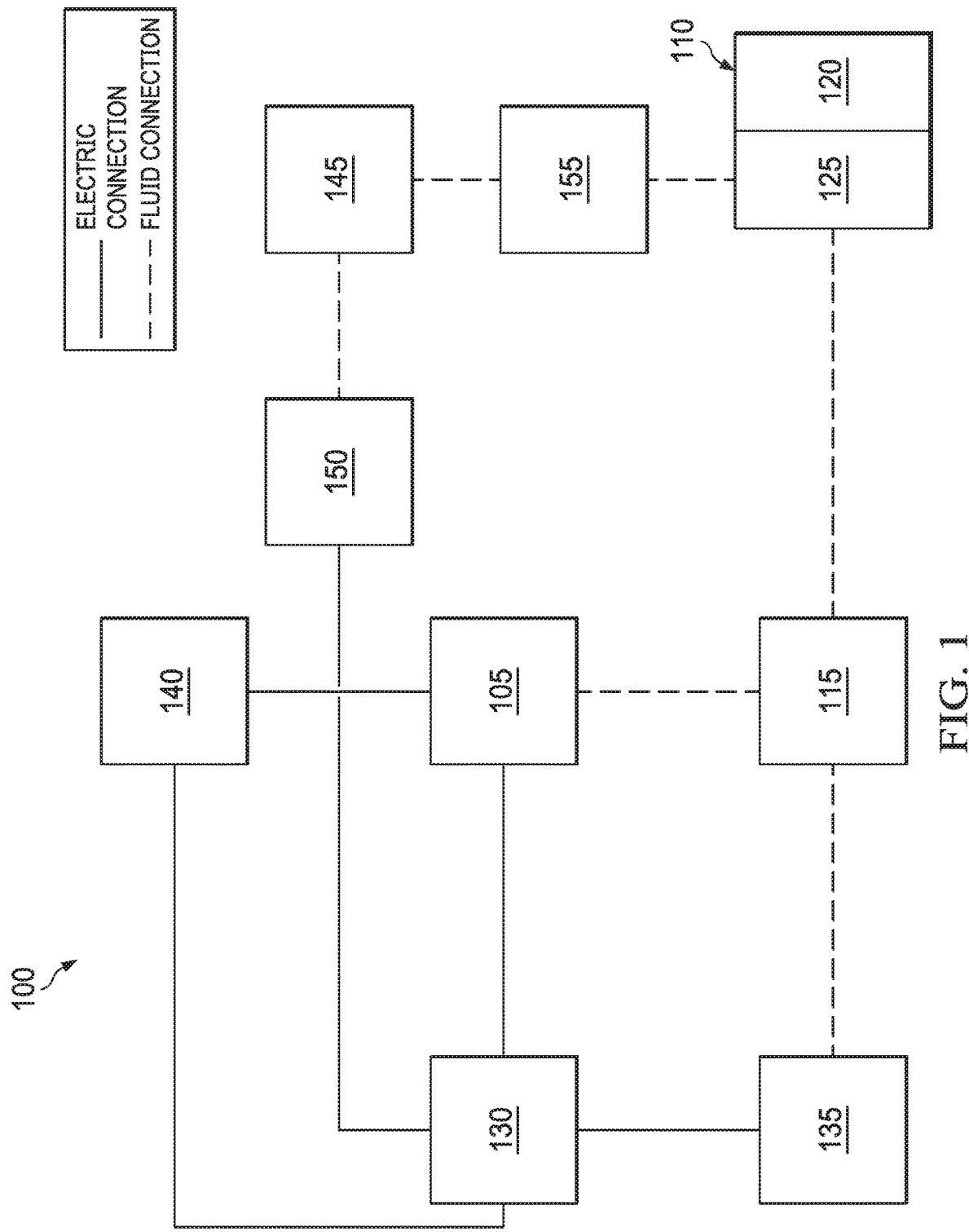
FIG. 1 is a block diagram of an example embodiment of a therapy system that can provide negative-pressure treatment and instillation treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Continuing with FIG. 1, the therapy system 100 may include a source or supply of negative pressure, such as a reduced pressure source or negative-pressure source 105, and one or more distribution components. A distribution component may be detachable, disposable, reusable, or recyclable. A dressing, such as a conformable dressing 110, and a fluid container, such as a container 115, are examples of distribution components that may be associated with some examples of the therapy system 100.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The process of reducing pressure may be described illustratively herein as "delivering," "distributing," or "generating" negative pressure, for example. In general, exudate and other fluid flow toward lower pressure along a fluid path. Thus, the term "downstream" typically implies a location in a fluid path relatively closer to a source of negative pressure or further away from a source of positive pressure. Conversely, the term "upstream" implies a location relatively further away from a source of negative pressure or closer to a source of positive pressure. Similarly, certain features may be described in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied to a tissue site in a sealed therapeutic environment can induce macro-strain and micro-strain in the tissue site. Negative pressure can also remove exudate and other fluid from a tissue site, which can be collected in the container 115.

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

As illustrated in the example of FIGS. 1-3C, the conformable dressing 110 may include a tissue interface layer or a carrier 120, and a plurality of filler elements or manifold members 125. Herein, references made to the carrier 120 may be similarly or analogously applicable to the interface layer, and references made to the manifold members 125 may be similarly or analogously applicable to the filler elements. In some embodiments, the conformable dressing 110 may include or be used with a sealing member 127 as part of the therapy system 100. The sealing member 127 may be capable of creating a sealed space 128 at a tissue site 129. An example of the tissue site 129 is shown as a knee in FIG. 2. In some embodiments, the conformable dressing 110 may be provided or used without the negative-pressure source 105 or other components of the therapy system 100.

In some embodiments, the sealing member 127 may provide a bacterial barrier and protection from physical trauma. The sealing member 127 may also be constructed from a material that can reduce evaporative losses and provide a fluid seal between two components or two environments, such as between a therapeutic environment and a local external environment. The sealing member 127 may comprise or consist of, for example, an elastomeric film or membrane that can provide a seal adequate to maintain a negative pressure at a tissue site for a given negative-pressure source. The sealing member 127 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the sealing member 127 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The sealing member 127 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, TEGADERM® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the sealing member 127 may comprise INSPIRE 2301 having an MVTR (upright cup technique) of 2600 g/m$^2$/24 hours and a thickness of about 30 microns.

An attachment device 126 may be used to attach the sealing member 127 to an attachment surface, such as undamaged epidermis, a gasket, or a cover. The attachment device 126 may take many forms. For example, an attachment device 126 may be a medically-acceptable, pressure-sensitive adhesive configured to bond the sealing member 127 to epidermis around a tissue site. In some embodiments, for example, some or all of the sealing member 127 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of the attachment device 126 may include a double-sided tape, paste, hydrocolloid, hydrogel, silicone gel, or organogel.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110 and the sealed space 128 through the sealing member 127. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the dressing 110, for example. The controller 130 is also preferably configured to receive one or more input signals, such as a feedback signal, and programmed to modify one or more operating parameters based on the input signals.

Sensors, such as the first sensor 135 and the second sensor 140 may be any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

In some embodiments, the controller 130 may receive and process data from one or more sensors, such as the first sensor 135. The controller 130 may also control the operation of one or more components of the therapy system 100 to manage the pressure delivered to the dressing 110 or components of the dressing 110. In some embodiments, controller 130 may include an input for receiving a desired target pressure and may be programmed for processing data relating to the setting and inputting of the target pressure to be applied to the dressing 110. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the dressing 110.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution, such as saline, to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

Further, in some embodiments, the controller 130 may receive and process data, such as data related to instillation solution provided to the dressing 110. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution.

For example, the controller 130 may manage fluid distributed from the solution source 145 to dressing 110 or components of the dressing 110. In some embodiments, fluid may be instilled to a tissue site by applying a negative pressure from the negative-pressure source 105 to reduce the pressure at the tissue site and drawing solution into the dressing 110. In some embodiments, solution may be instilled to a tissue site by applying a positive pressure from the positive-pressure source 150 to move solution from the solution source 145 to the dressing 110. Additionally or alternatively, the solution source 145 may be elevated to a height sufficient to allow gravity to move solution into dressing 110.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

Figure 2:
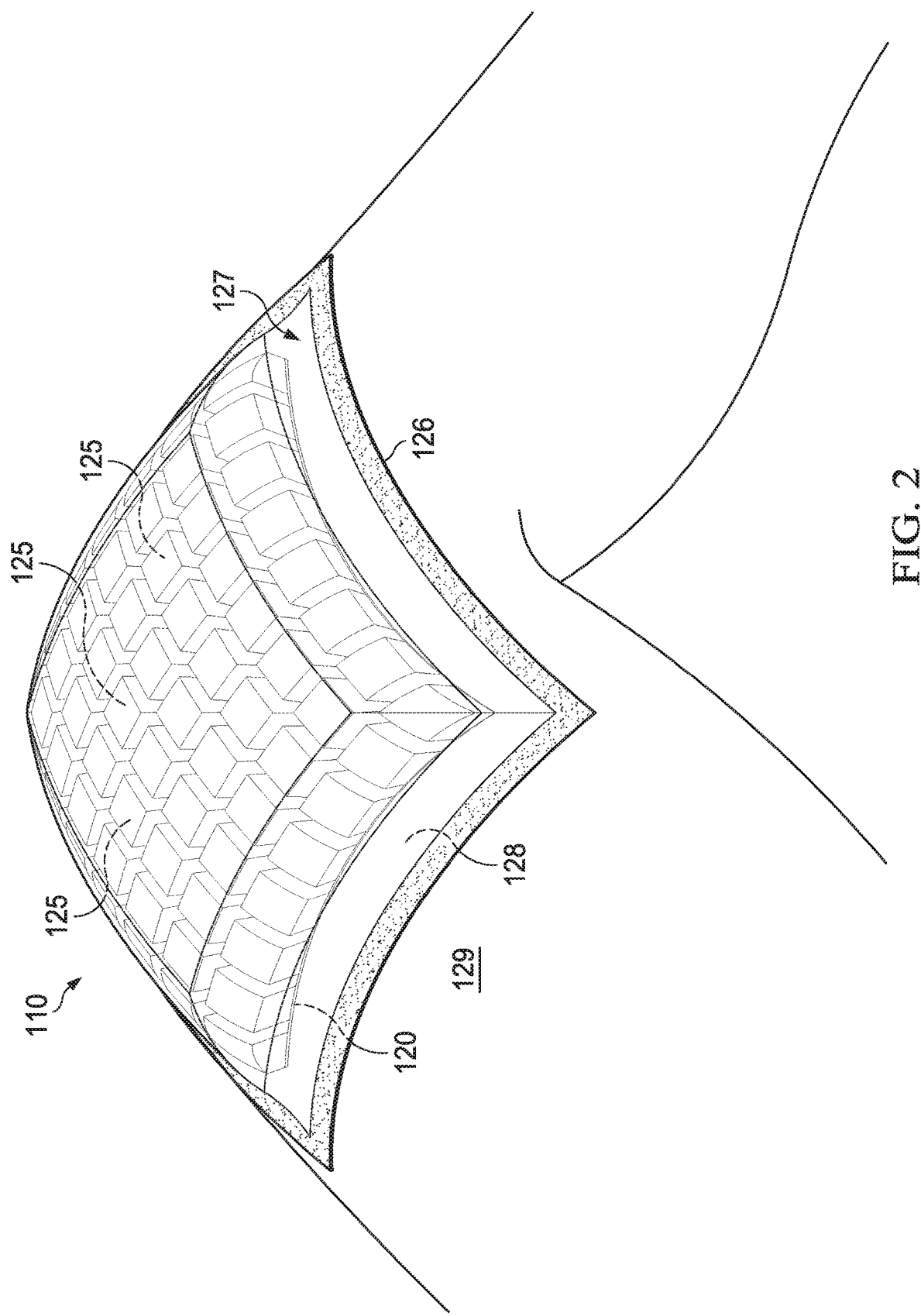
FIG. 2 is a perspective view of an example embodiment of a dressing suitable for use with the therapy system of FIG. 1 and shown deployed at an example tissue site.
Figure 3A:
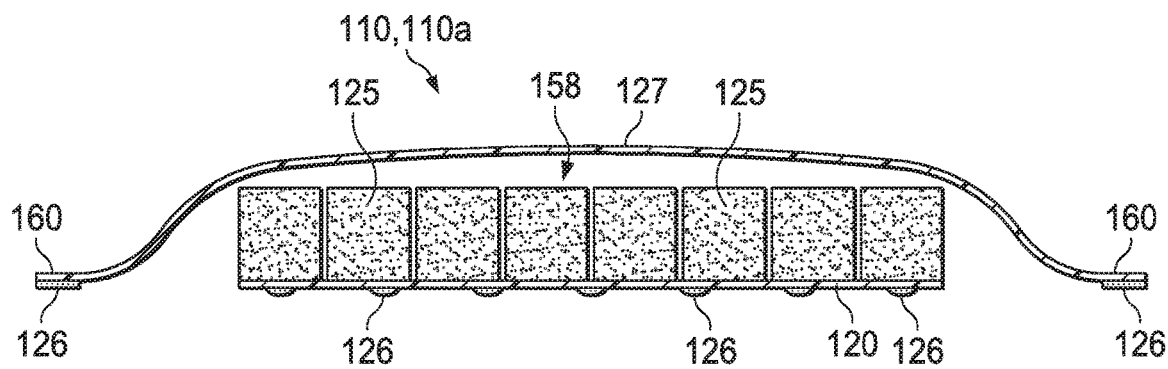
FIG. 3A is a side, cut-away view of another example embodiment of a dressing suitable for use with the therapy system of FIG. 1.
Figure 3B:
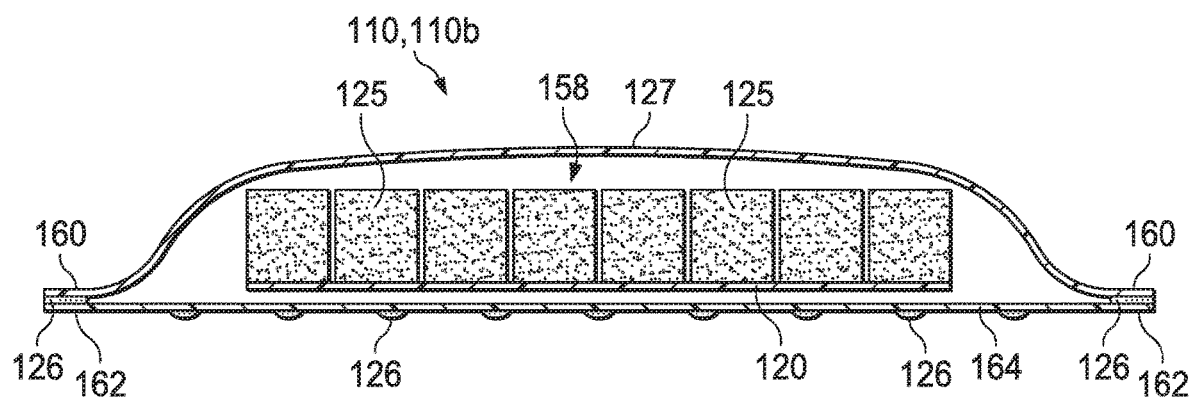
FIG. 3B is a side, cut-away view of yet another example embodiment of a dressing suitable for use with the therapy system of FIG. 1.
Figure 3C:
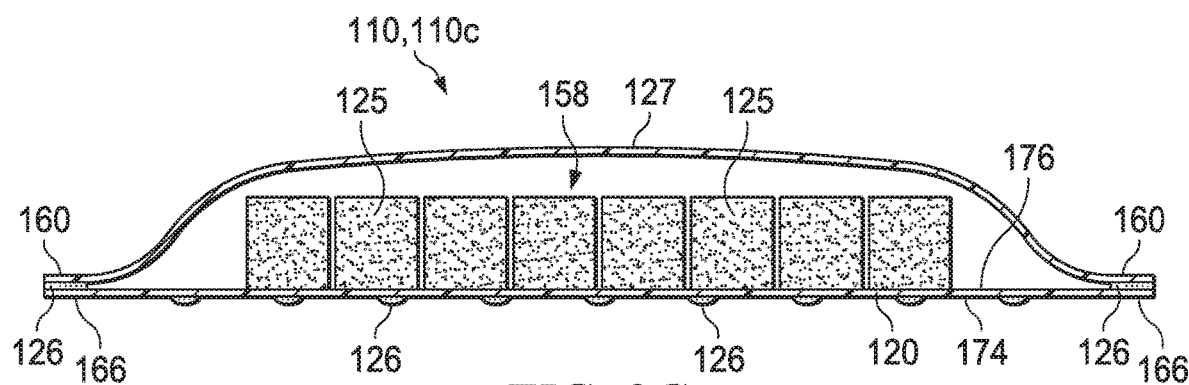
FIG. 3C is a side, cut-away view of yet another example embodiment of a dressing suitable for use with the therapy system of FIG. 1.

Referring to the example embodiments of FIGS. 3A-C, the dressing 110 may be configured, by way of example and without limitation, as a dressing 110a, a dressing, 110b, or a dressing 110c. As illustrated in FIG. 3A, the dressing 110a may include the sealing member 127 positioned to cover a dressing filler 158. The dressing filler 158 may include the manifold members 125 and the carrier 120. Although the dressing filler 158 is shown in FIGS. 3A-3C as part of the dressing 110, the dressing filler 158 may itself be referred to as a dressing in some embodiments, such as, for example, when the dressing filler 158 is used without the sealing member 127. The attachment device 126 may be coupled to or configured to be coupled to at least a periphery 160 of the sealing member 127. In some embodiments, the attachment device 126 may be coating covering an entire surface of the sealing member 127 that is configured to face the tissue site 129. The attachment device 126 may be configured to couple the sealing member 127 to tissue at or around the tissue site 129 to provide the sealed space 128. The manifold members 125 and the carrier 120 may be disposed in the sealed space 128 as shown in FIG. 2. The attachment device 126 may also be optionally positioned on a side of the carrier 120 configured to face the tissue site 129 to assist with deployment and positioning of the carrier 120 and other components of the dressing 110*a* at the tissue site 129.

As illustrated in FIG. 3B, the dressing 110*b* may include the sealing member 127 positioned to cover the dressing filler 158 including the manifold members 125 and the carrier 120. The attachment device 126 may be coupled to or configured to be coupled between at least a periphery 160 of the sealing member 127 and a periphery 162 of a base layer 164. In other embodiments, the periphery 160 of the sealing member 127 and the periphery 162 of the base layer 164 may be coupled by a heat bond, flame lamination, or other suitable device or method. The sealing member 127 and the base layer 164 may form an enclosure surrounding or encapsulating the manifold members 125 and the carrier 120. The base layer 164 may be formed from a fluid permeable material and/or a material including perforations or fenestrations configured to provide fluid communication relative to the tissue site 129. The attachment device 126 may also be optionally positioned on a side of the base layer 164 configured to face the tissue site 129 to assist with deployment and positioning of the base layer 164 and other components of the dressing 110*b* at the tissue site 129.

By way of example, suitable materials for the base layer 164 may include, without limitation, a medical grade 2-way or 4-way stretch fabric, such as INTERDRY™, available from Milliken and Company of Spartanburg, South Carolina, or LYCRA™, available from Koch Industries of North Carolina. Other suitable materials may include, without limitation, an elastic polyurethane fiber or fabric, elastane, spandex, a polyurethane film, silicone, silicone with an elastic scrim layer, or hydrocolloid.

As illustrated in FIG. 3C, the dressing 110*c* may include the sealing member 127 positioned to cover the manifold members 125 and the carrier 120. The attachment device 126 may be coupled to or configured to be coupled between at least a periphery 160 of the sealing member 127 and a periphery 166 of the carrier 120. In other embodiments, the periphery 160 of the sealing member 127 and the periphery 166 of the carrier 120 may be coupled by a heat bond, flame lamination or other suitable device or method. The sealing member 127 and the carrier 120 may form an enclosure surrounding or encapsulating the manifold members 125 and the carrier 120.

Referring to FIGS. 4-6B, the dressing filler 158 may include a plurality of the manifold members 125 and the carrier 120. Herein, the manifold members 125 may also be referred to as filler elements 125 including similar or analogous features, and the carrier 120 may also be referred to as a tissue interface layer 120 including similar or analogous features. Each of the manifold members 125 may include a first surface 168 and a second surface 170. The first surface 168 may be separated from the second surface 170 by a thickness 172 and a perimeter wall 173 extending along or around the thickness 172 between the first surface 168 and the second surface 170. The first surface 168 of the manifold members 125 may face opposite the second surface 170.

Figure 5A:
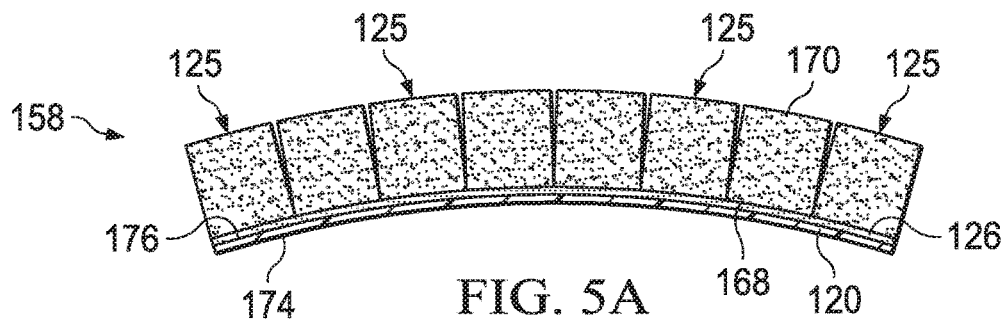
FIG. 5A is a side view of an example embodiment of a dressing filler illustrating an example embodiment of an attachment device.
Figure 5B:
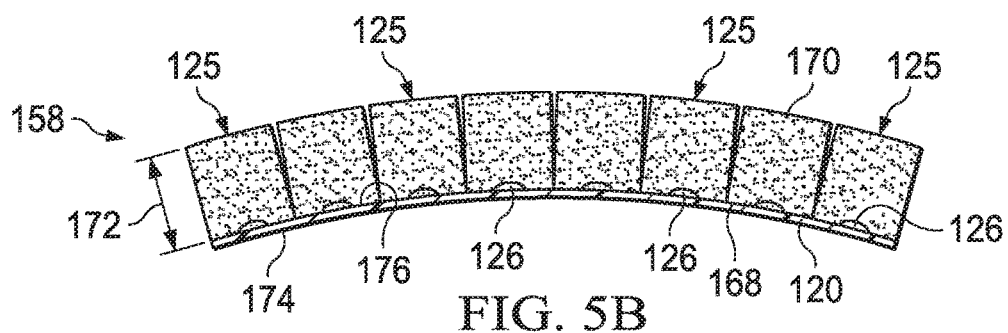
FIG. 5B is a side view of another example embodiment of a dressing filler illustrating another example embodiment of an attachment device.

The carrier 120 may include a first side 174 and a second side 176. The first side 174 of the carrier 120 may be configured to be positioned facing the tissue site 129. The second side 176 of the carrier may be positioned opposite the first side 174 of the carrier 120 and configured to be facing outward or away from the tissue site 129. The first surface 168 of each of the manifold members 125 may be coupled to the second side 176 of the carrier 120 as shown in FIGS. 5A-5B. One or more of the manifold members 125 may be individually moveable relative to one another when coupled to the second side 176 of the carrier 120.

The manifold members 125 may be coupled to the carrier 120 by the attachment device 126 illustrated in FIGS. 5A-5B. In some embodiments, the attachment device 126 may be a continuous or discontinuous layer or connecting surface extending fully between or along a contact surface between the manifold members 125 and the carrier 120 as shown in FIG. 5A. In other embodiments, the attachment device 126 may be provided as separate connecting dots, points, portions, or segments positioned between or along the contact surface between the manifold members 125 and the carrier 120 as shown in FIG. 5B, which may enhance or increase an amount of stretch or expansion that is possible between the manifold members 125. In other embodiments, the manifold members 125 may be coupled to the carrier 120 by other suitable methods including, without limitation, flame lamination, adhesive bonding, and welding.

The carrier 120 and the manifold members 125 may be manufactured in roll format or in any suitable shape to fit a particular tissue site. A sacrificial backing layer may be used during manufacture to support the manifold members 125 as they are coupled to the carrier 120. In some embodiments, a manifold layer may be coupled to the carrier 120 and the manifold layer may be subsequently kiss-cut to a depth of 100% or through an entire thickness of the manifold layer to form the manifold members 125. In some embodiments, a manifold layer may be cut to a depth of 90% to form the manifold members 125 with 10% of the thickness 172 measured from the first surface 168 of the manifold members 125 coupled to each other or one another for support.

In some embodiments, the carrier 120 may include a stretchable material having elastic properties. The stretchable material may be configured to stretch in at least one direction, and may be formed as a layer or sheet. In some embodiments, the carrier 120 may be configured to stretch in at least one direction up to about 50 percent in length such that the carrier 120 has a stretched length that is up to about 1.5 times longer than a relaxed length in at least one direction.

By way of example, suitable materials for the carrier 120 may include, without limitation, a medical grade 2-way or 4-way stretch fabric, such as INTERDRY™, available from Milliken and Company of Spartanburg, South Carolina, or LYCRA™, available from Koch Industries of North Carolina. A 2-way stretch fabric may be configured to stretch in one direction, and a 4-way stretch fabric may be configured to stretch in two directions. Other suitable materials may include, without limitation, an elastic polyurethane fiber or fabric, elastane, spandex, a polyurethane film, silicone, or silicone with an elastic scrim layer. Fenestrations may be disposed through the carrier layer 120 to enhance or to provide elastic properties or stretch. The fenestrations may additionally enhance or provide fluid permeability through the carrier layer 120.

Figure 6A:
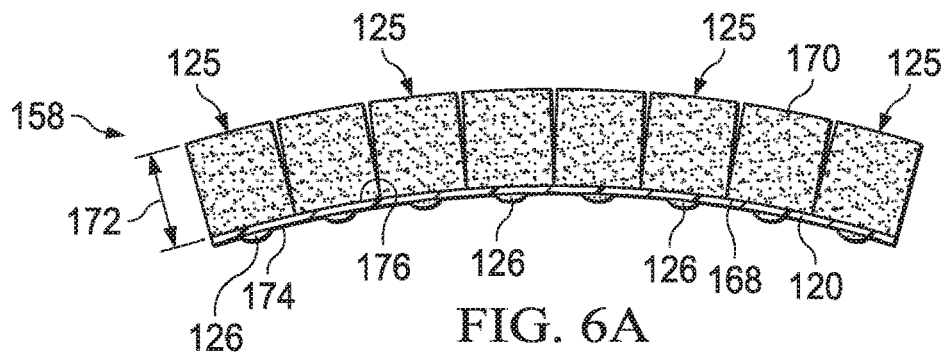
FIG. 6A is a side view of an example embodiment of a dressing filler positioned in a relaxed state.
Figure 6B:
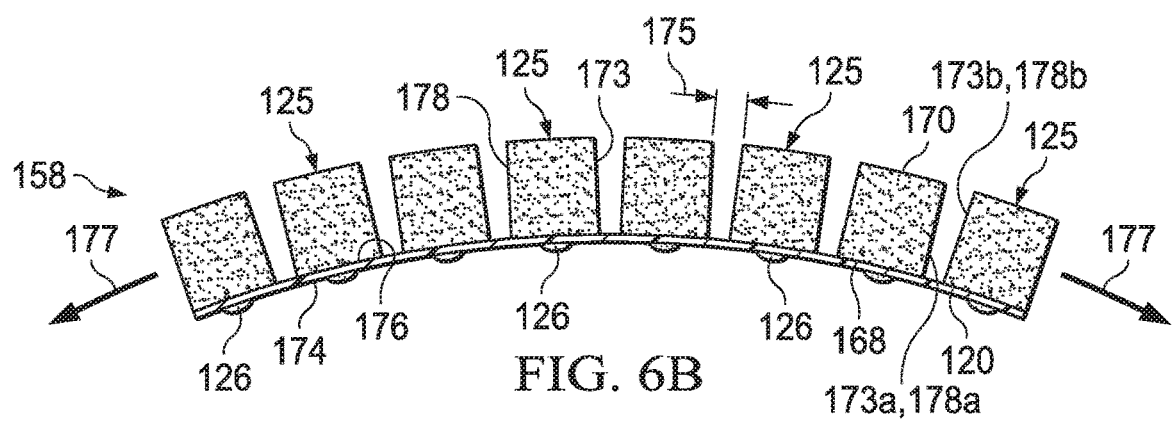
FIG. 6B is a side view of the dressing filler of FIG. 6A positioned in an expanded state or a stretched state.

The carrier 120 may be expandable between a relaxed state shown in FIG. 6A and an expanded state or a stretched state shown in FIG. 6B. A direction of stretch, expansion, or contraction of the carrier 120 may be coplanar to the material, fabric, sheet, or film that may form the carrier 120. For example, a direction 177 of stretch or expansion shown in FIG. 6B may lie along or in the same plane as the carrier 120. The direction 177 in FIG. 6B additionally provides an example of 2-way stretch described above, which is along one direction or line. An example of 4-way stretch described above would additionally include stretch along another direction or line extending into and out of the page of FIG. 6B, for example.

A separation distance 175 between a first perimeter wall 173a of one of the manifold members 125 and a second perimeter wall 173b of another of the manifold members 125 may be greater in the expanded state or stretched state than the relaxed state. Similarly, the separation distance 175 between a first exterior border 178a of one of the discrete manifold members 125 and a second exterior border 178b of another of the discrete manifold members 125 may be greater in the expanded state or the stretched state than the relaxed state. Further, in some embodiments, the first side 174 of the carrier 120 may optionally include the attachment device 126, such as an adhesive, to assist with placement and positioning of the carrier at the tissue site 129. Although illustrated in FIG. 6A-6B as dots, portions, or separate points, the attachment device 126 may be configured as a continuous or discontinuous layer in other embodiments.

In some embodiments, the manifold members 125 may be discrete manifold members 125. For example, one or more of the plurality of discrete manifold members 125 may be isolated or detached from each other or one another. In some embodiments, the perimeter wall 173 of the manifold members 125 may define an exterior border 178 that separates the manifold members 125 from each other or one another. Further, in some embodiments, one or more of the perimeter walls 173 of the manifold members 125 may be separated from each other or one another along the entire thickness 172 extending from the first surface 168 of the manifold members 125 to the second surface 170.

In other embodiments, less than 10 percent of the thickness 172 of one or more of the manifold members 125 may be coupled to the thickness 172 of another of the manifold members 125. In such an embodiment, less than 10 percent of the thickness 172 measured from the first surface 168 of one or more of the manifold members 125 may be coupled to a corresponding amount of the thickness 172 measured from the first surface 168 of another of the manifold members 125. Upon deployment at the tissue site 129, the manifold members 125 in this embodiment may be configured to stretch apart or tear apart from each other or one another.

Further, in some embodiments, the manifold members 125 may include or be formed from blocks of a porous material, such as, for example, foam, that may be configured to communicate fluid. A manifold in this context may comprise or consist essentially of a device for collecting or distributing fluid. For example, a manifold may be adapted to receive negative pressure from a source and to distribute negative pressure, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways, such as channels, may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the manifold members 125 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the manifold members 125 may also vary according to needs of a prescribed therapy. For example, the tensile strength of foam may be increased for instillation of topical treatment solutions. The 25% compression load deflection of the manifold members 125 may be at least 0.35 pounds per square inch, and the 65% compression load deflection may be at least 0.43 pounds per square inch. In some embodiments, the tensile strength of the manifold members 125 may be at least 10 pounds per square inch. The manifold members 125 may have a tear strength of at least 2.5 pounds per inch. In some embodiments, the manifold members 125 may be foam comprised of polyols such as polyester or polyether, isocyanate such as toluene diisocyanate, and polymerization modifiers such as amines and tin compounds. In some examples, the manifold members 125 may be reticulated polyurethane foam such as found in GRANUFOAM™ dressing or V.A.C. VERAFLO™ dressing, both available from Kinetic Concepts, Inc. of San Antonio, Texas.

The thickness 172 of the manifold members 125 may vary according to needs of a prescribed therapy. For example, the thickness 172 of the manifold members 125 may be decreased to reduce tension on peripheral tissue. The thickness 172 of the manifold members 125 can also affect the conformability of the manifold members 125. In some embodiments, the thickness 172 of the manifold members 125 may be between about 20 millimeters to about 35 millimeters. Further, in some embodiments, one or more of the manifold members 125 may have a three-dimensional size between about 8 cubic millimeters to about 12 cubic millimeters. Decreasing the size of the manifold members 125 may increase the resolution and conformability of the dressing 110 or the dressing filler 158.

The manifold members 125 may be either hydrophobic or hydrophilic. In an example in which the manifold members 125 may be hydrophilic, the manifold members 125 may also wick fluid away from the tissue site 129, while continuing to distribute negative pressure to the tissue site 129. The wicking properties of the manifold members 125 may draw fluid away from the tissue site 129 by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the manifold members 125 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones.

Figure 7A:
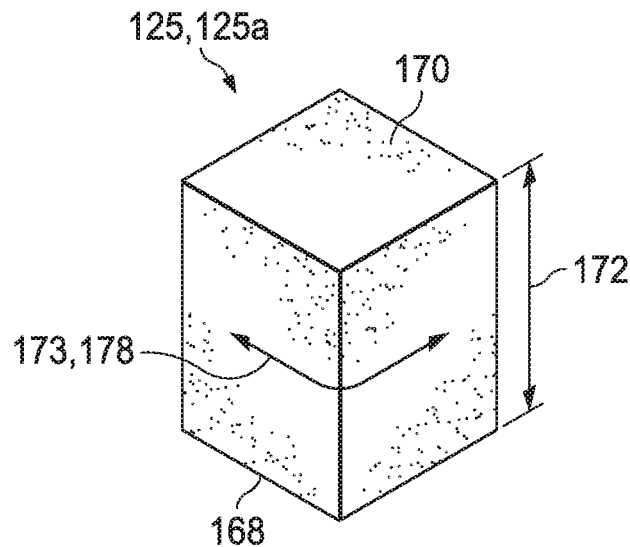
FIGS. 7A-7D are perspective views of multiple example embodiments of a manifold member or filler element suitable for use with a dressing filler or dressing according to this specification.
Figure 7B:
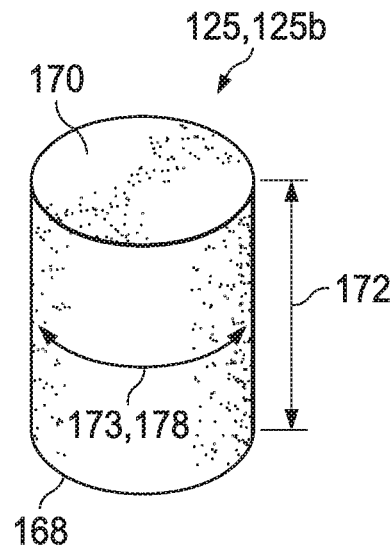
Figure 7C:
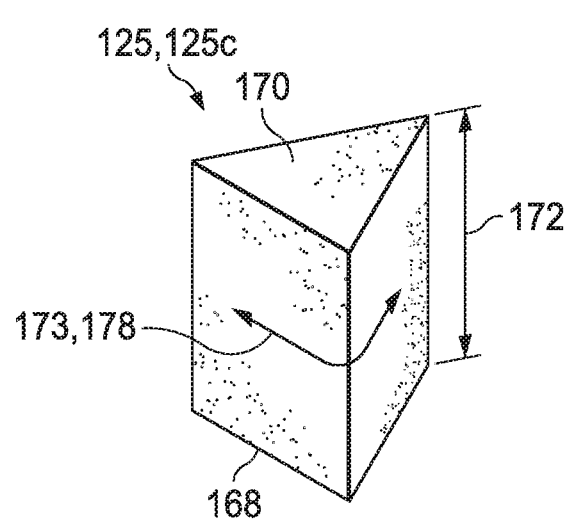
Figure 7D:
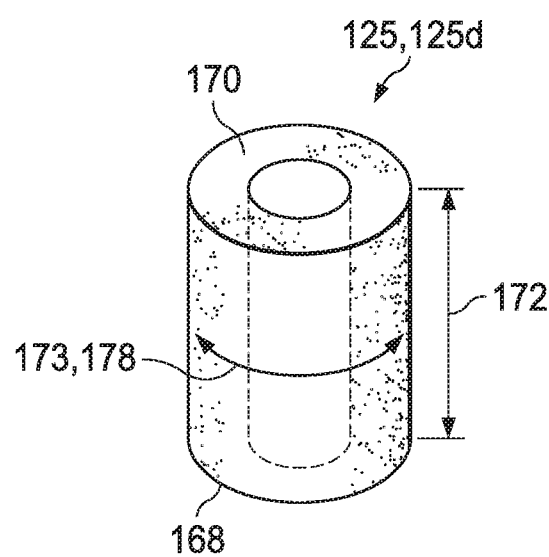

Referring to FIGS. 7A-8B, the manifold members 125 may have the same shape or a different shape and may take many forms, sizes, or thicknesses, depending on a variety of factors, such as the type of treatment being implemented or the nature and size of a tissue site. For example, the size and shape of the manifold members 125 may be adapted to the contours of deep and irregular shaped tissue sites. Any or all of the surfaces of the manifold members 125 may have an uneven, coarse, or jagged profile. In some embodiments, one or more of the manifold members 125 may be a manifold member 125a formed in the shape of a cube having a square cross-section as shown in FIG. 7A. In another embodiment, one or more of the manifold members 125 may be a manifold member 125b formed in the shape of a cylinder having a circular cross-section as shown in FIG. 7B. In another embodiment, one or more of the manifold members 125 may be a manifold member 125c having a triangular cross-section as shown in FIG. 7C. In another embodiment, one or more of the manifold members 125 may be a manifold member 125d formed in the shape of a cylinder and having an aperture disposed longitudinally through and between opposing surfaces of the cylinder as shown in FIG. 7D.

Figure 4:
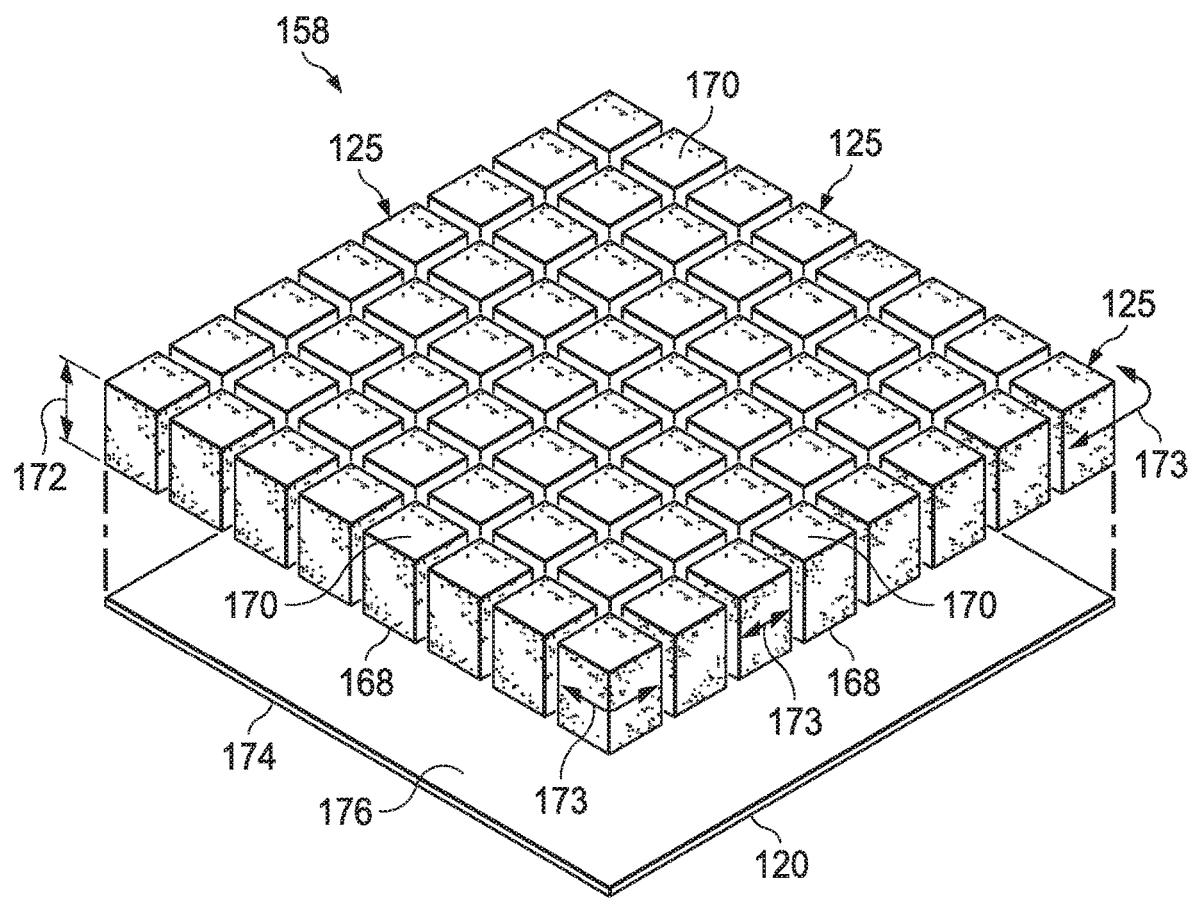
FIG. 4 is a perspective, exploded view of an example embodiment of a dressing filler suitable for use as a dressing or with a dressing according to this specification.
Figure 8A:
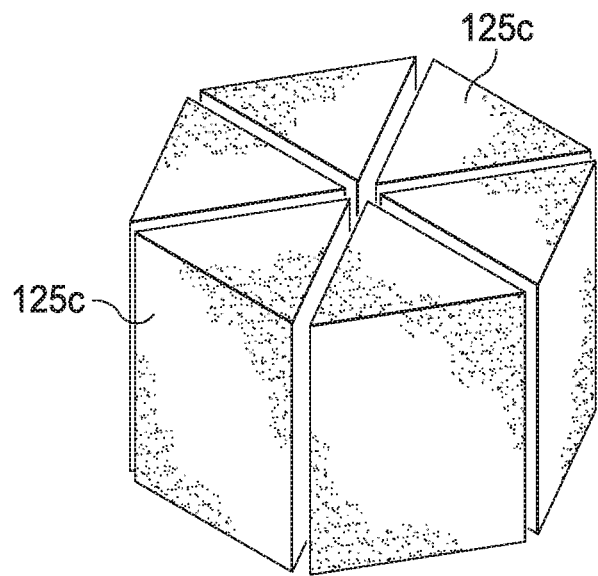
FIGS. 8A-8B are perspective views of multiple example embodiments of a pattern or configuration of manifold members or filler elements element suitable for use with a dressing filler or dressing according to this specification.
Figure 8B:
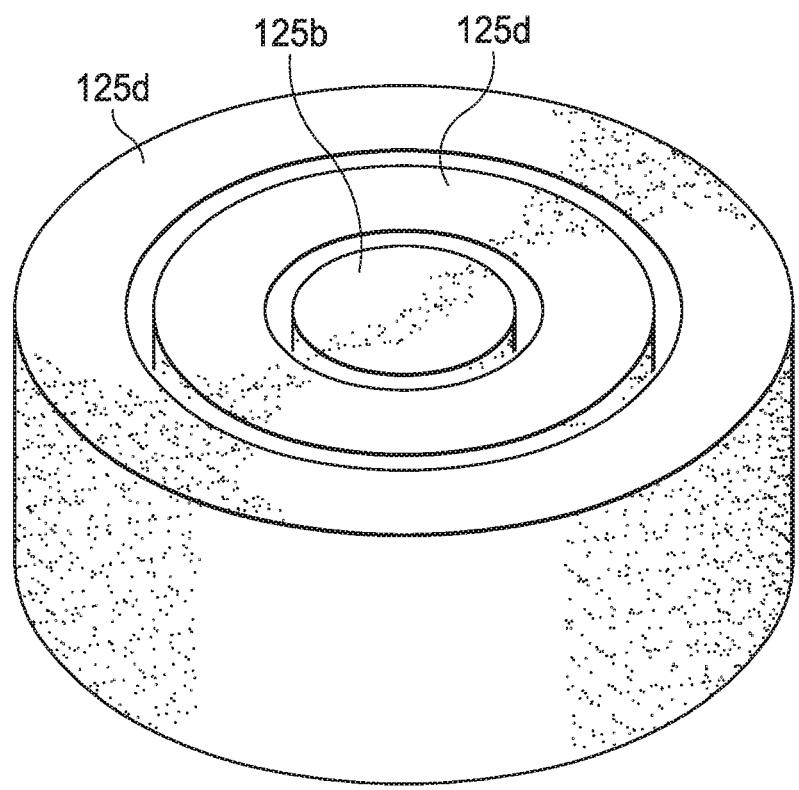
Figure 9:
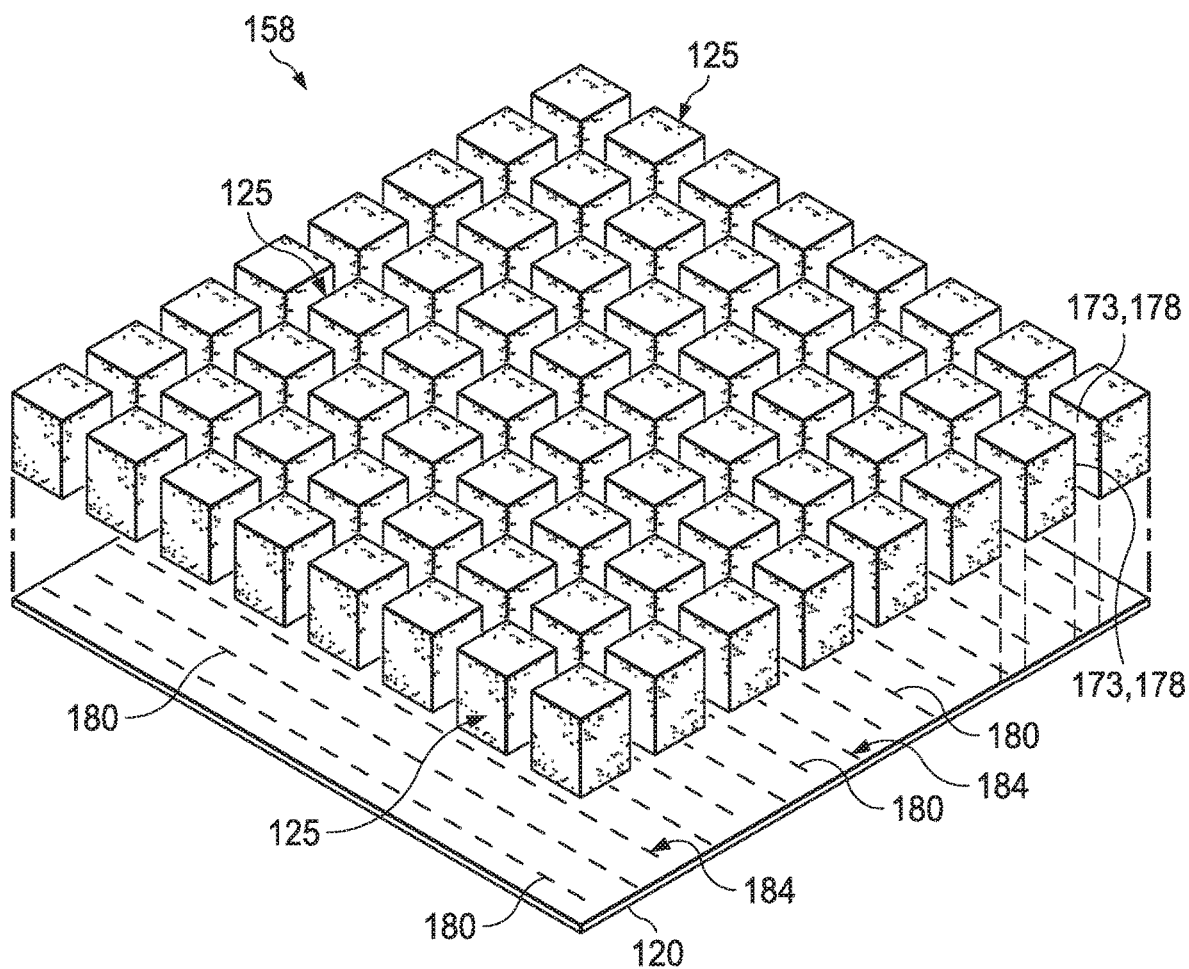
FIG. 9 is a perspective, exploded view of another example embodiment of a dressing filler suitable for use as a dressing or with a dressing according to this specification.

In addition to variations in the size and shape of each of the manifold members 125, the manifold members 125 may be arranged or positioned relative to each other on the carrier 120 in a variety of patterns. In some embodiments, the manifold members 125, 125a, 125b, 125c, 125d, or a manifold member of another shape, may be arranged in a matrix of rows and columns as shown in FIGS. 2, 4, and 9. In other embodiments, each of the manifold members 125 may be arranged to form different patterns or shapes to suit the anatomy of a particular tissue site. For example, the manifold members 125c having the triangular shape may be arranged in hexagonally shaped pattern as shown in FIG. 8A. Further, in other embodiments, different sizes of the manifold members 125b and 125d may be nested or arranged in a concentric circular pattern as shown in FIG. 8B.

Figure 10A:
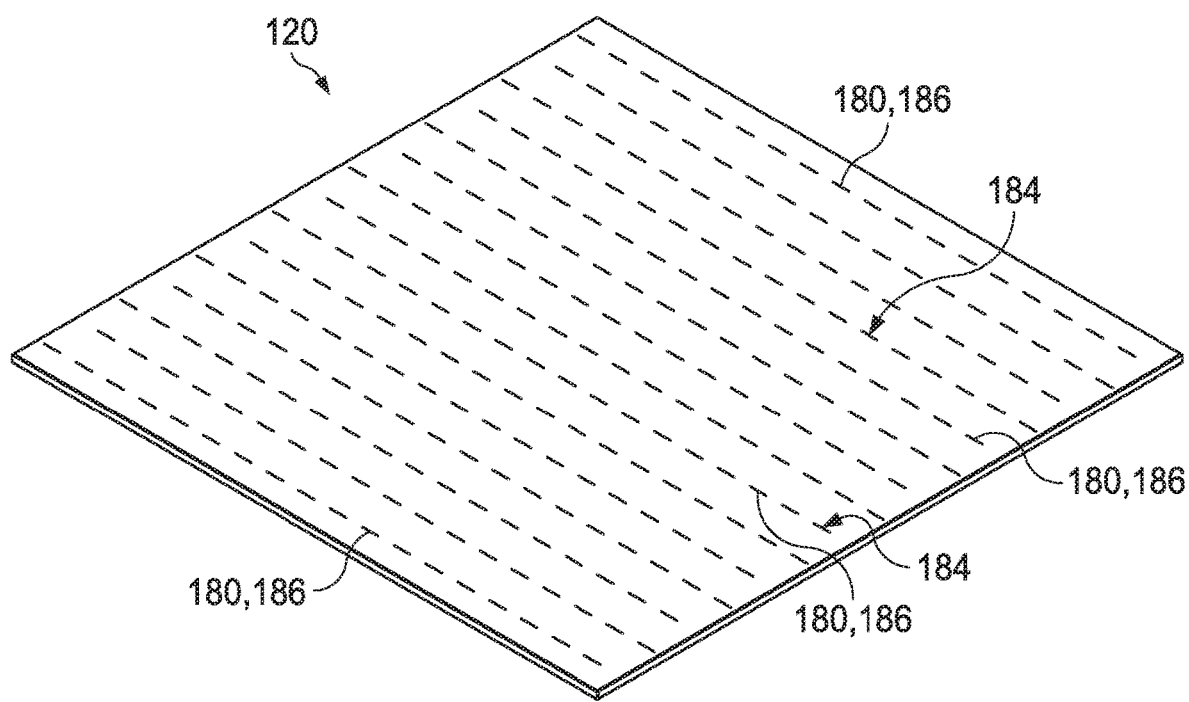
FIG. 10A is a perspective view of an example embodiment of a carrier or tissue interface layer illustrating an example embodiment of fenestrations disposed through the carrier or tissue interface layer.
Figure 10B:
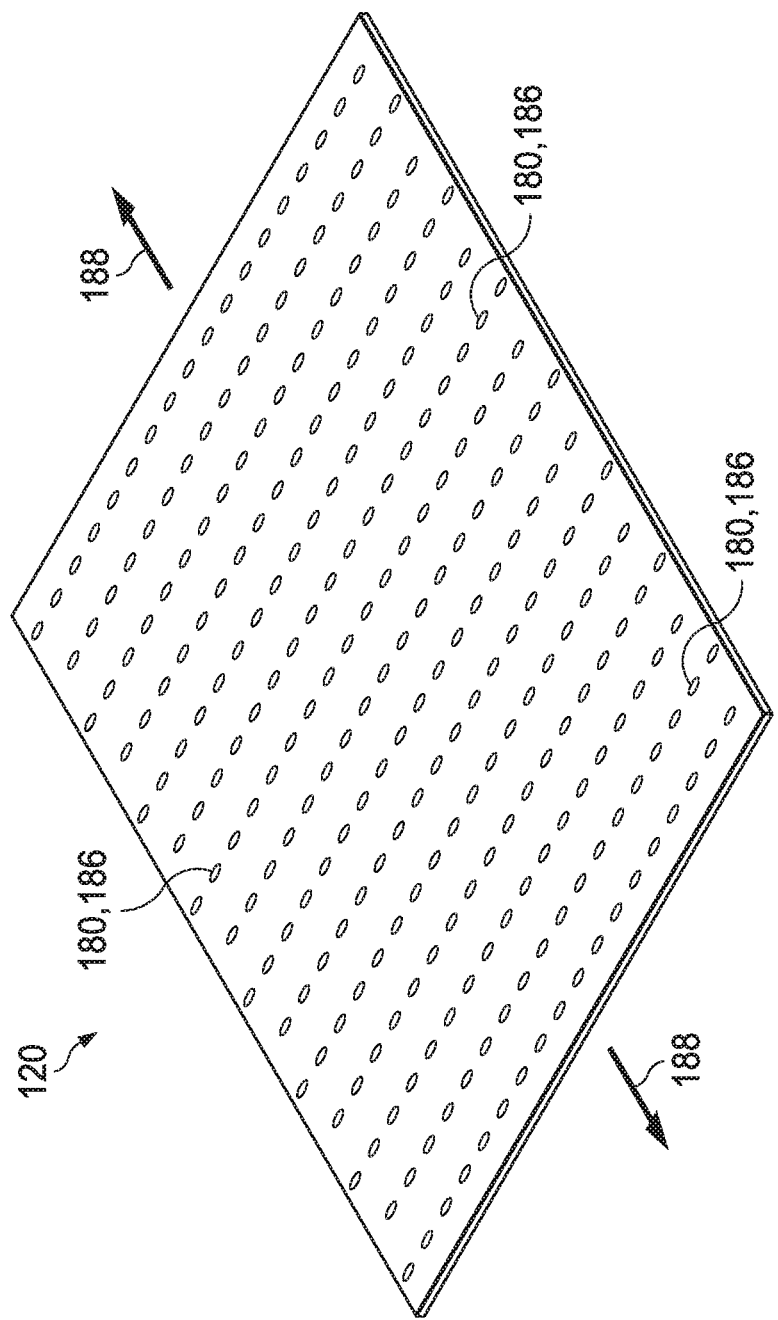
FIG. 10B is a perspective view of the carrier or tissue interface layer of FIG. 10A, illustrating stretch or expansion of the carrier and deformation of the fenestrations as a tensile force is applied to the carrier.

Referring FIGS. 9-10B, in some embodiments, the carrier 120 may include a plurality of fenestrations 180 disposed through the carrier 120. The fenestrations 180 may be, for example, holes, apertures, slits, or perforations formed through the carrier 120 in any suitable manner. The fenestrations 180 may enhance fluid permeability through the carrier 120. In some embodiments, the fenestrations 180 may be aligned or oriented lengthwise or longitudinally across the carrier 120 to form one or more separable perforations 184 on or through the carrier 120. The separable perforations 184 may provide a sizing guide that may be separated, torn, or cut to size the carrier 120 and the dressing filler 158 for the tissue site 129. For example, the separable perforations 184 may be positioned between the perimeter walls 173 or the exterior border 178 of the manifold members 125 to permit separation, tearing, or cutting to occur between the manifold members 125. Such a configuration may reduce or eliminate the possibility of particulate contamination from occurring at the tissue site 129 from shavings, trimmings, or waste that may be created after the dressing filler 158 is sized.

In some embodiments, the fenestrations 180 and the separable perforations 184 may enhance or promote expansion or stretch of the carrier 120. Herein, the fenestrations 180 may also be referred to as an expandable element 186.

In some embodiments, the carrier 120 may be formed from a non-stretchable material and the fenestrations 180 or the expandable element 186 may be configured to promote expansion of the non-stretchable material forming the carrier 120. For example, the fenestrations 180 or the expandable element 186 may be configured to deform and to provide stretch or expansion when a tensile force 188 is applied to the carrier 120 as shown in FIG. 10B. Herein, a non-stretch material may be any material considered in the art to be rigid, resistant to stretch, or to have reduced elasticity compared to materials designed to have elastic properties, such as those described above for other embodiments of the carrier 120.

In operation, the dressing filler 158 may be placed within, over, on, or otherwise proximate to a tissue site, such as the tissue site 129. If the tissue site is a wound, for example, the dressing filler 158 may partially or completely fill the wound, or be placed over the wound. The sealing member 127 may be positioned over or covering the dressing filler 158 and sealed to an attachment surface near a tissue site. For example, the sealing member 127 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

Figure 11A:
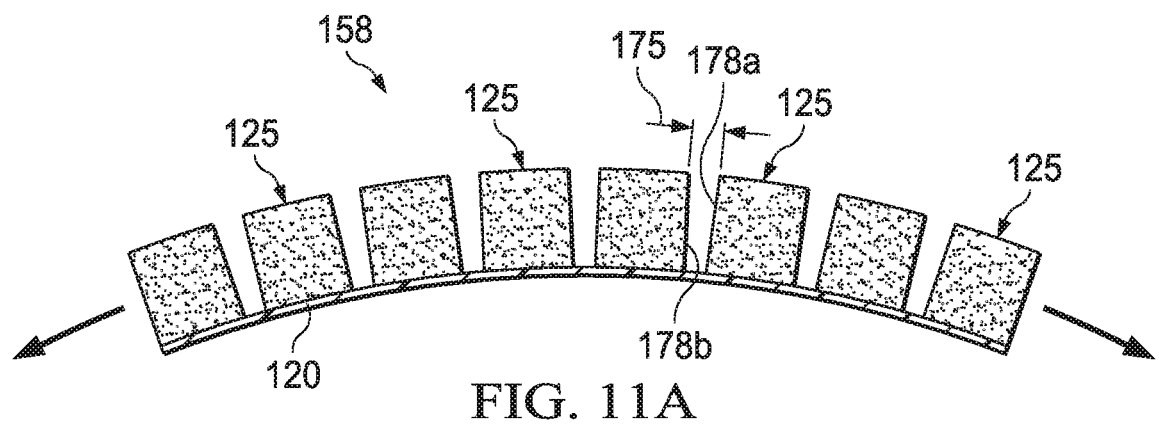
FIG. 11A is a side view of an example embodiment of a dressing filler positioned in a stretched or expanded state.

A method is also described herein, wherein in some example embodiments a method for treating a tissue site may include providing the conformable dressing 110 comprising the plurality of discrete manifold members 125 coupled to the stretchable carrier 120. The plurality of discrete manifold members 125 may be separated from one another along the exterior border 178. Further, the method may include positioning the conformable dressing 110 into conformity with tissue at the tissue site 129. At least a portion of the stretchable carrier 120 may be positioned in the stretched state, as shown, for example, in FIG. 11A, when the conformable dressing 110 is conformed to the tissue site 129. Further, the method may include covering the conformable dressing 110 with the sealing member 127 to form the sealed space 128 at the tissue site 129. Further, the method may include applying reduced pressure to the sealed space 128.

Figure 11B:
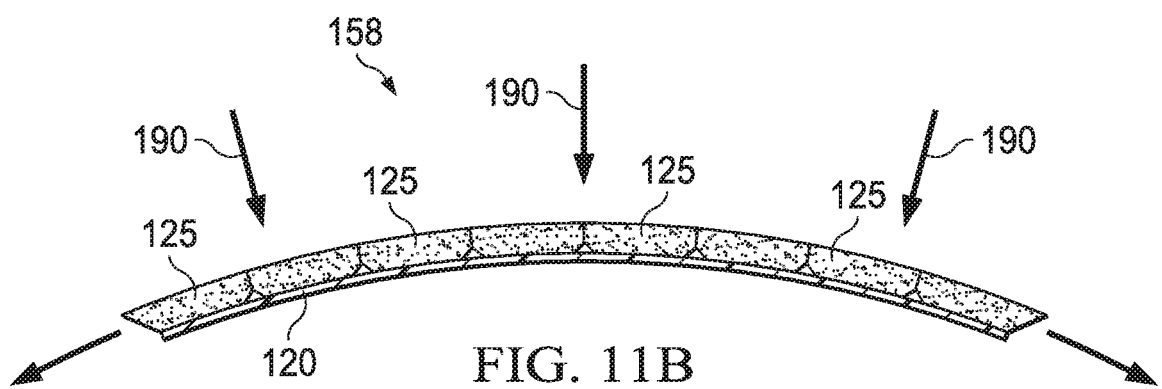
FIG. 11B is a side view of the stretched or expanded dressing filler of FIG. 11A illustrated with reduced pressure applied thereto.

One or more of the plurality of discrete manifold members 125 may be individually movable relative to one another when coupled to the stretchable carrier 120. Further, the plurality of discrete manifold members 125 may be entirely separated from one another along the exterior border 178. For example, in some embodiments, the plurality of discrete manifold members 125 may comprise detached blocks of porous material. Further, the plurality of discrete manifold members 125 may collapse into contact with one another as shown in FIG. 11B when a reduced pressure 190 is applied, thereby closing at least a portion of the separation distance 175 between the plurality of discrete manifold members 125.

Further, the stretchable carrier 120 may be stretchable between the relaxed state and the stretched state. The separation distance 175 between the first exterior border 178a of one of the discrete manifold members 125 and the second exterior border 178b of another of the discrete manifold members 125 may be greater in the stretched state than the relaxed state.

Further, positioning the conformable dressing 110 may include tearing or cutting through the stretchable carrier 120 between the plurality of discrete manifold members 125 to size the conformable dressing 110 for the tissue site 129. In some embodiments, positioning the conformable dressing 110 may include tearing or cutting through the separable perforations 184 in the stretchable carrier 120 to size the conformable dressing 110 for the tissue site 129.

The systems, apparatuses, and methods described herein may provide significant advantages. The configuration of the manifold members 125 and the carrier 120 may enhance the ability of the dressing 110 and the dressing filler 158 to conform to the tissue site 129, to contour to complex geometries, and to allow for articulation of limbs without causing pain, discomfort, or hindered healing. For example, the manifold members 125 are capable of moving independently with the carrier 120 as the carrier is stretched and conformed to the tissue site 129. The conformability of the dressing 110 and the dressing filler 158 may accommodate tissues sites contoured or shaped in multiple directions, and may additionally reduce shearing forces across the tissue site 129, prevent dislodgement of the dressing 110 and the dressing filler 158 from the tissue site 129, and provide enhanced articulation and movement at the tissue site 129.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A conformable dressing for treating a tissue site, comprising:
   a plurality of discrete manifold members, each discrete manifold member including a first surface and a second surface, the first surface separated from the second surface by a thickness and a perimeter wall extending along or around the thickness;
   a carrier including a first side configured to be positioned facing the tissue site and a second side positioned opposite the first side, the carrier expandable between a relaxed state and an expanded state; and
   an attachment device comprising a plurality of separate adhesive points configured to separately couple the first surface of each of the plurality of discrete manifold members to the second side of the carrier such that a distance between each of the plurality of discrete manifold members and a distance between each of the plurality of adhesive points increases in the expanded state;
   wherein the plurality of discrete manifold members comprises detached blocks of porous material.

2. The dressing of claim 1, wherein at least two discrete manifold members of the plurality of discrete manifold members are isolated from one another.

3. The dressing of claim 1, wherein at least two discrete manifold members of the plurality of discrete manifold members are individually movable relative to one another when coupled to the second side of the carrier.

4. The dressing of claim 1, wherein at least one discrete manifold member of the plurality of discrete manifold members comprises foam.

5. The dressing of claim 1, wherein the plurality of discrete manifold members comprises a porous material configured to communicate fluid.

6. The dressing of claim 1, wherein the perimeter wall of each of the plurality of discrete manifold members defines an exterior border separating the plurality of discrete manifold members from one another.

7. The dressing of claim 1, wherein the thickness is between 20 millimeters to 35 millimeters.

8. The dressing of claim 1, wherein one or more of the plurality of discrete manifold members have a three-dimensional size between 8 cubic millimeters to 12 cubic millimeters.

9. The dressing of claim 1, wherein one or more of the perimeter walls of the plurality of discrete manifold members are separated from one another along the entire thickness extending from the first surface to the second surface.

10. The dressing of claim 1, wherein the first surface of the plurality of discrete manifold members faces opposite the second surface.

11. The dressing of claim 1, wherein the discrete manifold members in the plurality of discrete manifold members have a same shape.

12. The dressing of claim 1, wherein the plurality of discrete manifold members have a different shape.

13. The dressing of claim 1, wherein the discrete manifold members in the plurality of discrete manifold members are arranged in a matrix of rows and columns.

14. The dressing of claim 1, wherein the plurality of discrete manifold members are arranged in concentric circles.

15. The dressing of claim 1, wherein the first side of the carrier comprises an adhesive, and wherein the second side of the carrier is configured to be positioned facing outward from the tissue site.

16. The dressing of claim 1, wherein a separation distance between a first perimeter wall of one of the discrete manifold members and a second perimeter wall of another of the discrete manifold members is greater in the expanded state than the relaxed state.

17. The dressing of claim 1, wherein the carrier comprises a stretchable material having elastic properties.

18. The dressing of claim 17, wherein the stretchable material is configured as a layer.

19. The dressing of claim 1, wherein the carrier comprises a stretchable material configured to stretch in at least one direction.

20. The dressing of claim 1, wherein the carrier is configured to stretch in at least one direction up to 50 percent in length.

21. The dressing of claim 1, wherein the carrier comprises a non-stretchable material and an expandable element configured to promote expansion of the carrier.

22. The dressing of claim 21, wherein the non-stretchable material of the carrier is configured as a layer, and the expandable element comprises a plurality of fenestrations disposed through the carrier, wherein the plurality of fenestrations are configured to deform when a tensile force is applied to the carrier.

23. The dressing of claim 22, wherein the plurality of fenestrations are aligned to form separable perforations on the carrier.

24. The dressing of claim 1, wherein the carrier further comprises a plurality of separable perforations disposed through the carrier.

25. The dressing of claim 24, wherein the separable perforations are positioned between the perimeter walls of the plurality of discrete manifold members.

26. A system for treating a tissue site with reduced pressure, comprising:
- a conformable dressing according to claim 1;
- a sealing member configured to cover the dressing and to create a sealed space at the tissue site; and
- a reduced pressure source configured to be coupled in fluid communication with the sealed space.

27. A dressing filler for treating a tissue site, comprising:
- a plurality of filler elements, each filler element including a first surface and a second surface opposite the first surface and separated from the first surface by a thickness; and
- a tissue interface layer including a first side configured to be positioned facing the tissue site and a second side positioned opposite the first side, the tissue interface layer expandable between a relaxed state and an expanded state; and
- an attachment device comprising a plurality of separate adhesive points configured to separately couple the first surface of each of the plurality of filler elements to the second side of the tissue interface layer such that a distance between each of the plurality of filler elements and a distance between each of the plurality of adhesive points increases in the expanded state;
- wherein the plurality of filler elements comprises detached blocks of porous material.

28. The dressing filler of claim 27, wherein the thickness is between 20 millimeters to 35 millimeters.

29. The dressing filler of claim 27, wherein at least one filler element of the plurality of filler elements comprises foam.

30. The dressing filler of claim 27, wherein at least two filler elements of the plurality of filler elements are entirely separated from one another along the thickness extending from the first surface to the second surface.

31. The dressing filler of claim 27, further comprising a perimeter wall extending along the thickness between the first surface and the second surface of the plurality of filler elements, wherein the perimeter wall defines an exterior border separating the plurality of filler elements from one another.

32. The dressing filler of claim 27, wherein a separation distance between one of the filler elements and another of the filler elements is greater in the expanded state than the relaxed state.

33. The dressing filler of claim 27, wherein less than 10 percent of the thickness of at least one filler element of the plurality of filler elements is coupled to the thickness of another filler element of the plurality of filler elements.

34. The dressing filler of claim 33, wherein the first surface of the at least one filler element of the plurality of filler elements is coupled to the first surface of another filler element of the plurality of filler elements.

* * * * *